(12) United States Patent
Johnson et al.

(10) Patent No.: US 7,064,834 B2
(45) Date of Patent: Jun. 20, 2006

(54) METHOD FOR ANALYZING IMPURITIES IN CARBON DIOXIDE

(75) Inventors: Michael Clinton Johnson, Grand Island, NY (US); Carl Joseph Heim, Amherst, NY (US); John Fredric Billingham, Getzville, NY (US); Mark Leonard Malczewski, North Tonawanda, NY (US)

(73) Assignee: Praxair Technology, Inc., Danbury, CT (US)

( * ) Notice: Subject to any disclaimer, the term of this patent is extended or adjusted under 35 U.S.C. 154(b) by 353 days.

(21) Appl. No.: 10/350,307

(22) Filed: Jan. 22, 2003

(65) Prior Publication Data

US 2003/0197852 A1 Oct. 23, 2003

Related U.S. Application Data

(60) Provisional application No. 60/350,688, filed on Jan. 22, 2002.

(51) Int. Cl.
*G01N 21/00* (2006.01)
*G01N 15/02* (2006.01)

(52) U.S. Cl. ..................... 356/437; 356/336

(58) Field of Classification Search ............ 356/437, 356/336, 337, 338, 339, 340, 341, 342, 343, 356/37; 73/1.01, 1.02, 1.06, 23.2, 23.21, 73/23.22–23.42, 24.01–24.06, 25.01–25.05, 73/28.01–28.06, 29.01–29.02, 335.01–335.14, 73/29.03–29.05, 30.01–30.04, 31.01–31.07
See application file for complete search history.

(56) References Cited

U.S. PATENT DOCUMENTS

| | | | | |
|---|---|---|---|---|
| 3,787,122 A | * | 1/1974 | Lepper, Jr. ............... | 356/338 |
| 3,854,321 A | * | 12/1974 | Dahneke .................. | 73/28.01 |
| 4,806,171 A | * | 2/1989 | Whitlock et al. ........... | 134/7 |
| 4,868,398 A | | 9/1989 | Mulcey et al. | |
| 4,894,529 A | * | 1/1990 | Borden et al. ............. | 356/338 |
| 5,027,642 A | * | 7/1991 | Wen et al. ................ | 73/23.2 |
| 5,065,794 A | * | 11/1991 | Cheung .................... | 137/883 |
| 5,254,719 A | * | 10/1993 | Holzhauer et al. .......... | 560/78 |
| 5,265,031 A | * | 11/1993 | Malczewski ............... | 702/24 |

(Continued)

OTHER PUBLICATIONS

Maximilian A. Biberger, et al., *Photoresist and Photoresist Residue Removal with Supercritical $CO_2$—A Novel Approach to Cleaning Wafers*, Semiconductor Fabtech 239-243 (12th ed. 2000).

(Continued)

*Primary Examiner*—Layla G. Lauchman
*Assistant Examiner*—Juan D. Valentin, II
(74) *Attorney, Agent, or Firm*—Iurie A. Schwartz (57) ABSTRACT

This invention relates to methods and systems for detecting contaminants that can precipitate and deposit on a workpiece during a carbon dioxide application, especially contaminants that are already present and dissolved in the fresh carbon dioxide fed to the application. One aspect of this invention includes a method of detecting contaminants dissolved in a carbon dioxide stream, including the steps of sampling at least a portion of the carbon dioxide stream to form a carbon dioxide sample; modifying at least one physical condition of the carbon dioxide sample to form an aerosol that includes gaseous carbon dioxide and at least one suspended contaminant; and detecting the number of particles of suspended contaminant in at least a portion of the carbon dioxide sample with at least one particle counter. A system for continuously detecting contaminants dissolved in a carbon dioxide stream is also described.

21 Claims, 4 Drawing Sheets

U.S. PATENT DOCUMENTS

| | | | |
|---|---|---|---|
| 5,278,626 A * | 1/1994 | Poole et al. | 356/337 |
| 5,298,967 A * | 3/1994 | Wells | 356/338 |
| 5,369,033 A | 11/1994 | Di Milia et al. | |
| 5,665,902 A * | 9/1997 | Wang et al. | 73/28.01 |
| 5,777,726 A | 7/1998 | Krone-Schmidt | |
| 5,865,901 A * | 2/1999 | Yin et al. | 134/2 |
| 5,968,371 A * | 10/1999 | Verdegan et al. | 73/53.05 |
| 5,992,216 A * | 11/1999 | Wang et al. | 73/28.01 |
| 5,996,420 A * | 12/1999 | Lee | 73/23.41 |
| 6,016,686 A * | 1/2000 | Thundat | 73/23.2 |
| 6,122,954 A | 9/2000 | Bowers | |
| 6,244,120 B1 | 6/2001 | Maeda | |
| 6,276,169 B1 | 8/2001 | Bowers et al. | |
| 6,284,022 B1 | 9/2001 | Sachweh et al. | |
| 6,289,715 B1 * | 9/2001 | Gilbert et al. | 73/31.02 |
| 6,639,671 B1 * | 10/2003 | Liu | 356/336 |
| 6,676,768 B1 * | 1/2004 | Fillipi et al. | 73/28.01 |
| 6,786,075 B1 * | 9/2004 | Radke et al. | 73/24.06 |

OTHER PUBLICATIONS

Thomas Kosic & Jeff L. Palser, *Carbon Dioxide Meets the Challenge of Precision Cleaning*, Solid State Tech. 1:7 (May 1998).

Kenneth E. Laintz, et al., *Solubility in Supercritical Fluid Cleaning* in Supercritical Fluid Cleaning Fundamentals, Technology and Applications 22-37 (John McHardy & Samuel P. Sawan eds., 1998).

Guo-Tang Liu & Kunio Nagahama, *Application of Rapid Expansion of Supercritical Solutions in the Crystallization Separation*, 35 Ing. Eng. Chem. Res. 4626-34 (1996).

M.J. Sepaniak, et al., *Microcantilever Transducers: A New Approach in Sensor Technology*, 74 Analytical Chemistry 568A (2002).

Richard R. Zito, $CO_2$ *Snow Cleaning of Optics: Curing the Contamination Problem*, Proc. of SPIE—The Int'l Soc'y for Optical Eng'g 4096 (2000).

\* cited by examiner

METHOD FOR ANALYZING IMPURITIES IN CARBON DIOXIDE

RELATED APPLICATION(S)

This application claims the benefit of U.S. Provisional Application No. 60/350,688, filed Jan. 22, 2002. The entire teachings of the above application is incorporated herein by reference.

BACKGROUND OF THE INVENTION

Carbon dioxide normally supplied to food and beverage customers must meet a set of purity specifications known as Enhanced Ingredient Grade (EIG). Carbon dioxide of this purity is sufficient for use in food and beverages, and most plants can produce it.

Some applications require carbon dioxide of higher purity than EIG. For example, supercritical fluid extraction and supercritical fluid chromatography require small amounts of higher purity carbon dioxide. Examples of the types of higher purity carbon dioxide include Supercritical Fluid Extraction (SFE) and Supercritical Fluid Chromatography (SFC) grades. These grades of carbon dioxide are generally supplied in cylinders.

Additional applications requiring high purity and ultra-high purity (UHP) carbon dioxide have recently been developed. These include pharmaceutical processing, semiconductor processing (photoresist removal and wafer cleaning), micro-electro-mechanical systems (MEMS) drying, and metal target cleaning.

In the past, several techniques have been used to measure impurities in carbon dioxide. One common technique is High Pressure Liquid Chromatography (HPLC). An example of this technique is described in Zito, R., "$CO_2$ Snow Cleaning of Optics: Curing the Contamination Problem," Proceedings of SPIE Vol. 4096 (2000). The method is time consuming, expensive, and may not be sensitive enough to detect the low levels of impurities present in UHP carbon dioxide. Further, since the nature of the contaminants in the carbon dioxide is often not known, it is difficult to design a HPLC technique that will detect all potential impurities contained in carbon dioxide.

Gravimetric methods are also currently used to determine the level of contamination contained in carbon dioxide. In one technique, a known sample volume of carbon dioxide is passed through or over a medium such as a preweighed filter used to capture solid contaminants. Alternatively, contaminants are collected in a small volume of solvent which is subsequently evaporated. The weight of contaminants is estimated by measuring the change in the mass of the filter or solvent's container. The weight of the carbon dioxide can be calculated by its flow rate or measuring the decrease in the weight of its storage cylinder. From these two measurements, the concentration of the contaminant can be calculated. Gravimetric techniques generally are labor intensive and done in a batch-mode fashion. This makes them unsuited for use in a continuous process, such as an on-line contaminant analysis.

U.S. Pat. No. 6,276,169 B1 discloses liquid carbon dioxide expanding through a primary nozzle to form a mixture of carbon dioxide snow and vapor. The contaminants contained in the liquid carbon dioxide are assumed to be trapped in the snow particles. This two-phase stream is then expanded through a secondary nozzle to produce a low density, low velocity stream. The solid carbon dioxide, with impurities, is collected at the exit of the nozzle while the carbon dioxide gas escapes. The collected frozen carbon dioxide is then heated to its sublimation point, driving off the carbon dioxide and leaving the impurities concentrated in the collection container. These impurities are then analyzed to determine their quantity and composition. For example, the carbon dioxide snow is deposited onto a high purity surface. As the carbon dioxide sublimes, the impurities are left on the surface. An ellipsometer also is used to gauge the thickness of the contamination layer on a wafer at various points, the wafer having been covered in the carbon dioxide snow collected from the nozzle. By averaging the thickness of the film over the entire wafer, a volume of contaminant is calculate which is used to estimate the impurity level. Since it collects and measures contaminants in a batch-wise fashion, this technique is not suited for continuous on-line analysis of contaminants.

U.S. Pat. No. 6,122,954 discloses measuring contaminants through the use of a surface acoustic wave (SAW) resonator. The basic idea of the SAW resonator is to measure the decrease in resonant frequency of a piezoelectric crystal onto which the contaminants deposit as a result of the sensor being at a lower temperature. Essentially, it acts as an extremely sensitive mass balance. Once the mass of the contaminant is known, its concentration can be determined. The SAW device is inefficient for measuring non-gaseous contaminants and it must be cleaned after it has sorbed a certain amount of material. SAW devices are similar to other piezoelectric techniques, but use a surface, rather than a bulk, oscillation in the crystal.

Therefore, a need exists for methods and systems suitable for analyzing impurities in carbon dioxide that reduce or minimizes the above mentioned problems.

SUMMARY OF THE INVENTION

Emerging applications often require ultra-pure carbon dioxide with lower contaminant levels than demanded by previous processes. The levels of contaminant in UHP carbon dioxide are so small, that most traditional detection mechanisms are unable to measure them.

This invention recognizes that at high pressure, UHP carbon dioxide often includes dissolved contaminants. A change in condition can cause the dissolved contaminants to precipitate, forming an aerosol of gaseous carbon dioxide and suspended contaminant particles. These suspended particles can be detected in order to monitor the dissolved contaminants.

This invention generally relates to the detection of contaminants dissolved in carbon dioxide. In one embodiment, the invention is directed to a method of detecting contaminants dissolved in a carbon dioxide stream, including the steps of a) sampling at least a portion of the carbon dioxide stream to form a carbon dioxide sample; b) modifying at least one physical condition of the carbon dioxide sample to form an aerosol that includes gaseous carbon dioxide and at least one suspended contaminant; and c) detecting the number of particles of suspended contaminant in at least a portion of the carbon dioxide sample with at least one particle counter.

In still another embodiment, this invention is direct to a method for monitoring contaminants in a carbon dioxide stream that is directed to a workpiece, including the steps of a) identifying a reference value, wherein said reference value indicates that the dissolved contaminants will precipitate and deposit onto the workpiece in acceptably low levels, by detecting the number of particles of at least a portion of the dissolved contaminants in a calibration process which includes the steps of i) sampling at least a portion of an acceptable carbon dioxide stream to form an acceptable carbon dioxide sample; ii) modifying the conditions of the acceptable carbon dioxide sample to form an aerosol of gaseous carbon dioxide and precipitated contaminants, whereby at least a portion of the contaminants are in the form of suspended droplets; and iii) detecting the number of particles of at least a portion of the acceptable carbon dioxide sample with at least one particle counter; thereby identifying said reference value; b) subsequently directing a carbon dioxide stream to the workpiece; c) sampling said carbon dioxide stream to identify at least one measured value, wherein said measured value indicates whether contaminants will precipitate from the carbon dioxide stream and deposit onto the workpiece in an acceptably low level, by detecting the number of particles of an essentially equal portion of the dissolved contaminants as employed to determine the reference value in a monitoring process which includes the steps of i) sampling at least a portion of said carbon dioxide stream to form a carbon dioxide sample; ii) modifying the conditions of the carbon dioxide sample to form an aerosol of gaseous carbon dioxide and precipitated contaminants; and iii) detecting the number of particles in the portion of the carbon dioxide sample with at least one particle counter; thereby identifying said measured values; and d) comparing the measured values with the reference value to determine the number of dissolved particles that will precipitate from the subsequently directed carbon dioxide and deposit onto the workpiece is an acceptably low level, thereby monitoring contaminants of the carbon dioxide stream.

This invention also relates to a system for continuously detecting contaminants dissolved in a carbon dioxide stream flowing through a solvent feed line, including: a) a sampling means for removing a sample stream, wherein said sample stream is at least a portion of the carbon dioxide stream flowing through the solvent feed line; b) a modification means in fluid communication with the sampling means, wherein said modification means modifies the conditions of the sample stream to form an aerosol of gaseous carbon dioxide and suspended contaminants; c) at least one contaminant measurement zone in fluid communication with the modification means; and d) at least one particle counting means, wherein said particle counting means can detect at least a portion of the suspended contaminants in the contaminant measurement zone with at least one particle counter.

A user of this invention can detect impurities dissolved in carbon dioxide, even impurities dissolved in UHP carbon dioxide. A user can also determine whether a stream of carbon dioxide has low enough levels of impurities so that its use in a carbon dioxide process will produce acceptable results.

A user of this invention can prevent the deposition of contaminants onto a workpiece during a carbon dioxide application, especially those contaminants already present in the fresh carbon dioxide fed to the process. This invention also provides for a method of measuring the actual concentration of contaminants dissolved in carbon dioxide. This is accomplished by correlating the number of particles of suspended contaminant from carbon dioxide of an unknown contaminant level, to those obtained from a carbon dioxide with a known contaminant level.

Since a user of this invention can detect contaminants dissolved in carbon dioxide, a user of this invention can also determine when action should be taken to remove at least a portion of the contaminants from the carbon dioxide so that the carbon dioxide contaminant level falls within an acceptable range.

Prior methods of detecting contaminants were primarily suited for batch-wise detection. This invention provides detection methods and systems which can continuously detect contaminants in carbon dioxide streams.

DETAILED DESCRIPTION OF THE INVENTION

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The present invention generally relates to applications that use carbon dioxide. Preferably, the application uses carbon dioxide at a pressure lower than about 10,000 psia. More preferably, the application uses carbon dioxide at a pressure less than about 4,000 psia. The invention is particularly well suited for applications that use carbon dioxide in a supercritical, critical, or subcritical phase. Carbon dioxide has a supercritical temperature of 31° C. and a supercritical pressure of 1070 psia, a triple point pressure and temperature of 75 psia and −57° C. respectively, and its sublimation temperature at ambient pressure is approximately −78° C.

Examples of applications which use carbon dioxide include electronics applications, such as photoresist stripping and deposition; pharmaceutical applications, such as nanoparticle formation; and the processing of micro-electro-mechanical systems (MEMS). Applications may also use carbon dioxide in a two-phase state, such as carbon dioxide snow cleaning applications. Snow cleaning applications typically expand carbon dioxide to close to ambient pressure in order to form solid carbon dioxide "snow" and carbon dioxide gas, which is then used in the cleaning applications.

This invention is particularly suited for an application that requires high purity carbon dioxide. Preferably, the application requires ultra-high purity carbon dioxide (UHP). As used herein, the term "ultra-high purity" refers to a composition that contains contaminants in concentrations of around 10 ppb by weight ($1 \times 10^{-6}$ wt. %) or less. Examples of ultra-high purity applications include MEMS cleaning and drying, the manufacture of high-quality optical devices, drug production, wafer cleaning, and others.

Contaminants in a carbon dioxide stream can include solid particles, such as small (e.g., microscopic) pieces of metal shed by machinery used in the carbon dioxide application. Generally, solid contaminants do not dissolve in high pressure or supercritical carbon dioxide.

The contaminants also can include non-volatile residue (NVR). As used herein, the term "non-volatile residue" refers to contaminants that are dissolved in the carbon dioxide and condense or precipitate following sublimation or evaporation of the carbon dioxide at room temperature and pressure. While the exact chemical composition of NVR often is unknown, examples include heavy organics ($C_{10+}$) such as aliphatic hydrocarbon-based heavy oils, halocarbons, and particulate matter that is soluble in carbon dioxide under certain conditions but not at atmospheric pressure and room temperature. Sources of NVR are compressor oils and elastomeric materials that have some solubility in liquid carbon dioxide and are commonly found in gasket and valve seat material.

The solubility of NVR contaminants in carbon dioxide is a strong function of density, which is in turn a function of temperature and pressure. At high pressures, the solvation functionality is not simple, but in general, high pressures and temperatures favor the solubility of NVRs in carbon dioxide. With decreases in temperature and pressure, the solubility of NVRs in carbon dioxide typically decreases. At ambient temperatures and pressures, for example, NVRs generally precipitate from the carbon dioxide, forming an aerosol of gaseous carbon dioxide and suspended particulate contaminants. The contaminant particles are believed to be mostly in the form of liquid droplets.

In processes utilizing liquid or supercritical carbon dioxide, the processing conditions of the carbon dioxide will typically change. These changes in conditions can cause NVR to exceed its solubility limit and precipitate from the carbon dioxide. These precipitated NVR particles or droplets can impinge the workpiece and deposit onto the surface, interfering with successful completion of the process. This is a particular concern for processes that have very high cleanliness requirements. Aerosol droplets and dissolved contaminants can not be filtered effectively from the carbon dioxide, if at all. Solid particles that do not dissolve in the carbon dioxide are less of a concern because they can be filtered from the carbon dioxide before it reaches the application.

For example, at some point in a cleaning process, the cleaning chamber is opened in order to remove the workpiece being cleaned. Often, this necessitates that the chamber environment be depressurized to atmospheric pressure. Any carbon dioxide still within the cleaning chamber will drop in pressure, causing dissolved contaminants to precipitate from the carbon dioxide and impinge or deposit on the previously clean workpiece.

If the process is a snow cleaning application, the expansion of liquid carbon dioxide can similarly cause dissolved contaminants to precipitate into the solid carbon dioxide snow. When the application is complete, the snow sublimes and deposits the NVR onto the workpiece.

Generally, EIG carbon dioxide may contain up to about 5 ppm NVR by weight. SFE and SFC carbon dioxide have been found to contain approximately 0.15 ppm NVR by weight, but even this level may be unacceptable for some applications. Preferably, UHP carbon dioxide contains no more than 10 ppb NVR by weight ($1 \times 10^{-6}$% by weight), and more preferably less than about 1 ppb by weight ($1 \times 10^{-7}$% by weight) for the emerging applications described above.

In one embodiment, the invention is directed to a method of detecting contaminants dissolved in a carbon dioxide stream, including the steps of a) sampling at least a portion of the carbon dioxide stream to form a carbon dioxide sample; b) modifying at least one physical condition of the carbon dioxide sample to form an aerosol that includes gaseous carbon dioxide and at least one suspended contaminant; and c) detecting the number of particles of suspended contaminant in at least a portion of the carbon dioxide sample with at least one particle counter.

Figure 1:
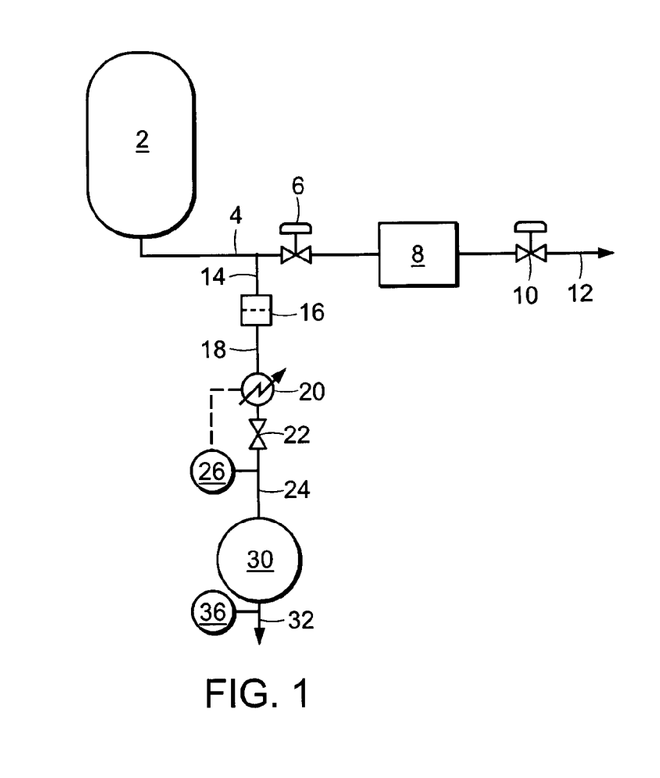
FIG. 1 is a schematic diagram illustrating one embodiment of the present invention, wherein the suspended particles are detected with a particle analyzer.
Figure 2:
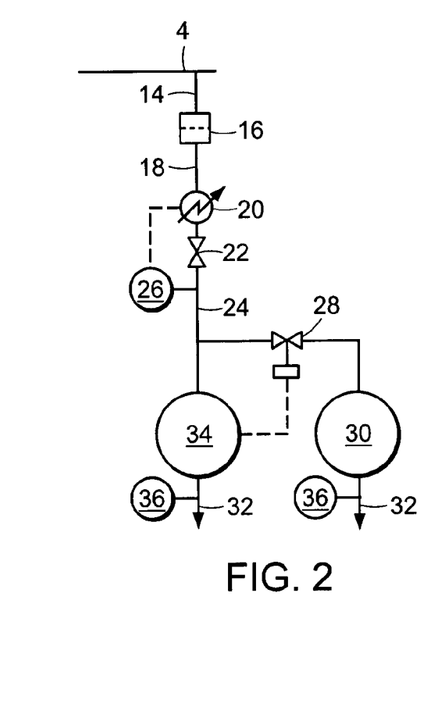
FIG. 2 is a schematic diagram illustrating one embodiment of the present invention, wherein a first analyzer prevents a particle analyzer from being overwhelmed by suspended particles.

This method is described with respect to FIG. 1. Shown in FIG. 1 is carbon dioxide source 2 and carbon dioxide stream 4. Carbon dioxide source 2 can be a gas cylinder or another source of carbon dioxide as known in the art. Preferably, carbon dioxide stream 4 is UHP grade of carbon dioxide (about 10 ppb by weight impurities; $1 \times 10^{-6}$ wt % impurities) or carbon dioxide which has been purified to a larger degree than that which can be obtained commercially. More preferably, carbon dioxide stream 4 contains less than 1 ppb by weight impurities ($1 \times 10^{-7}$ wt %). Carbon dioxide stream 4 contains contaminants, including dissolved contaminants, e.g., NVRs. Also, carbon dioxide stream 4 can be a two-phase flow of carbon dioxide, such as a mixture of carbon dioxide vapor and carbon dioxide snow used in a carbon dioxide snow cleaning application. Preferably, carbon dioxide stream 4 is at a pressure less than about 10,000 psia. More preferably, the pressure is less than about 4,000 psia.

Carbon dioxide stream 4 is directed through flow control valve 6 and into chamber 8, such as a chamber used in a wafer cleaning process. After processing, the carbon dioxide exits chamber 8 through flow control device 10 and vent 12. Vent 12 may exhaust the carbon dioxide to the atmosphere or to a carbon dioxide recycle system.

A portion of carbon dioxide stream 4 is diverted to form carbon dioxide sample 14. Carbon dioxide sample 14 can be formed continuously or at selected times. Carbon dioxide sample 14 can be passed through optional filter 16, such as, for example, a sintered metal filter, to remove solid contaminants and form filtered stream 18. For example, solid contaminants are filtered from carbon dioxide sample 14 so that they are not subsequently detected as dissolved contaminants which have precipitated, and thus inflate the particle count.

The condition of filtered carbon dioxide stream 18 (or carbon dioxide sample 14 if optional filter 16 is not present) is changed by passing it through optional heater 20 and pressure reduction device 22, which change the temperature and pressure of filtered carbon dioxide stream 18 so that at least a portion of the dissolved contaminants precipitate from the carbon dioxide. Pressure reduction device 22 can be a pressure reduction valve or a flow orifice. Alternatively, pressure reduction device 22 can precede optional heater 20.

Pressure reduction at pressure reduction device 22 causes at least a portion of the dissolved contaminants to precipitate, forming aerosol 24, which includes gaseous carbon dioxide and suspended contaminant droplets. Preferably, the pressure of aerosol 24 is sufficient so that it will continue to flow through the detection process and not stagnate. Preferably, the pressure of aerosol 24 is less than about 3,000 psia. More preferably, the pressure of aerosol 24 is less than about 1,065 psia. Most preferably, the pressure of aerosol 24 is about 14.7 psia.

The heat supplied by optional heater 20 is preferably sufficient to ensure that the carbon dioxide in aerosol 24 is completely in the vapor state. More preferably, the heat supplied is sufficient to ensure aerosol 24 has a temperature slightly above the sublimation or boiling point for carbon dioxide at the pressure of aerosol 24. If a portion of the carbon dioxide is in a liquid and/or solid phase, that portion will be subsequently detected as contaminant particles and inflate the contaminant detection results, making it more difficult to estimate the amount of contaminant contained in carbon dioxide stream 4. For example, an aerosol at a pressure of 50 psia preferably is above about −60° C. to ensure that there are no dry ice particles in the sample.

In one embodiment, the pressure of the carbon dioxide is reduced and its temperature adjusted to normal temperature and pressure (NTP). However, in some carbon dioxide applications, an absence of particles at normal temperature and pressure does not mean that condensation of contaminants will not occur in practice. For example, in snow cleaning applications, the temperature of the snow/gas mixture is approximately −78 C. At this temperature, the solubility of the contaminants of interest is expected to be lower than at normal temperature and pressure. For such applications in particular, it may be preferable to conduct the analysis as close to the sublimation temperature as is practically possible. This is to minimize the amount of carbon dioxide in a non-gaseous phase, and in turn minimize the amount of carbon dioxide detected as suspended particles.

However, some carbon dioxide contaminants may only be detectable at temperatures and pressures where it is unavoidable that part of the carbon dioxide be in a solid or liquid state. If the particular detection process demands such, the particle count can be reduced in order to correct for the particles of non-gaseous carbon dioxide detected. The practicality of the measurement will depend on the instrument and its environment. For example, condensation of moisture around the device may require that the analyzer be located in a dry enclosure, e.g., one purged with nitrogen.

In some embodiments, optional heater 20 may not be necessary as the carbon dioxide sample line may be small enough so that a sufficient amount of heat leaks from the surroundings to cause the carbon dioxide to completely enter the gas phase. This will be especially practical in applications with extended carbon dioxide flow lines and low carbon dioxide flow rates. In those cases, a simple approach is to form the aerosol at ambient temperature and a pressure which is just slightly higher than ambient in order to facilitate aerosol flow.

Optional aerosol measurement device 26, can measure some property of aerosol 24 after is has passed through optional heater 20 and/or pressure reduction device 22. For example, aerosol measurement device 26 can be a thermocouple, a pressure measuring device, a flow meter, or some combination thereof. Aerosol measurement device 26 can provide feedback to optional heater 20 and/or pressure reduction device 22 in order to ensure that aerosol 24 attains the desired temperature and pressure.

Optional filter 16 may be placed after optional heater 20, pressure reduction device 22, or both. Placing optional filter 16 after optional heater 20 and/or pressure reduction device 22 can be important if they are themselves sources of solid particulate contamination which could affect the particle detection. However, placing the filter after or during the formation of aerosol 24 may itself cause an erroneous particle count because optional filter 16 may capture or entrain a portion of the contaminant droplets formed upon the pressure reduction. An alternative solution is to correct the particle count by subtracting an "average" shed count measured using a clean gas source.

At least a portion of aerosol 24 is then directed to particle analyzer 30 where at least a portion of the suspended contaminants (believed to be liquid droplets) are detected. In a preferred embodiment, particle analyzer 30 uses a particle counter. As used herein, the term "particle counter" refers to a particle detection device which uses a single-particle detection technique to detect single particles.

Single-particle detection techniques detect particles by counting each individual particle or droplet. In light scattering particle counters, the single particle is passed through an incident beam. The particle scatters the light pulse. The resultant scattered light pulse is detected and analyzed. In order to generate a usable signal from a single particle, a very intense incident light source is used and a large fraction of the resulting light is analyzed.

Particle analyzer 30 can be a particle counter which counts the individual droplets or precipitated contaminant suspended in aerosol 24. One type of particle counter is a white-light particle counter. A white-light particle counter uses a halogen bulb or other incandescent light source to generate the incident beam. White-light particle counters can generally detect particles with diameters as small as about 0.5 µm.

A second type of particle counter uses a laser as the incident light source. These types of counters are collectively known as laser particle counters (LPCs). LPCs can use a solid-state laser diode to produce the incident light source. Solid-state laser diode counters generally run at a cool temperature and have fewer maintenance issues than other particle counters. LPCs are typically able to count and size individual particles down to 0.3 µm in diameter.

Since the amount of scattered light falls off as a $6^{th}$-power function of the particle radius, to detect individual particles down to about 0.05 µm in diameter, a more intense gas-powered laser is used to generate the incident light source from a gas, such as a mixture of helium and neon.

Different LPC-type particle counters have been designed to operate at various pressures such as 100–3000 psig, 40–150 psig, or atmospheric pressure, depending upon the application. Examples of these types of particle counters are those designed by Particle Measuring Systems, Inc., (Boulder, Colo.) such as the CGS-100, the HPGP-101, and the Lasair®-101 respectively.

In another preferred embodiment, particle analyzer 30 is a condensation nucleus counter (CNC). In CNCs, the particles are grown to a size that can scatter enough light off of a single particle to be easily detected even with a relatively low intensity source. This is accomplished by condensing a working fluid on the incoming particle such that when it enters the detection or viewing volume, it can be readily observed. The CNCs typically operate at atmospheric pressure.

The CNCs are unsuited for sizing the resulting particle because the condensation process grows each incoming particle to the same final diameter (typically 1–2 µm in diameter) upon reaching the detector. This disadvantage is offset by the ability of the CNC to count particles efficiently as small as 0.01 µm in diameter. This is about a factor of 5–10 improvement over the limit of detection (LOD) for LPC units. The improved detection limit is an advantage when sampling NVR droplets formed from low concentrations of dissolved material as the predominant particle size may fall below 0.1 µm in diameter.

In yet another preferred embodiment, a CNC is employed in parallel with a LPC. The CNC then effectively functions as a lower size "bin" of the LPC. By subtracting the results from the two counters, the fraction of particles between 0.01 and 0.1 µm in diameter can be determined.

After the suspended contaminant particles are counted, aerosol 24 exits particle analyzer 30 as exhaust stream 32, which can be vented to the atmosphere or passed to additional analytical processes. Optional flow meter 36 can measure the flow of the aerosol as it leaves the particle analyzer 30. Optional flow meter 36 can send a signal to pressure reduction device 22 or to another valve (not shown) which increases or decreases the amount of carbon dioxide stream 4 sampled.

In some embodiments of this invention, particle analyzer 30 can be positioned to sample dissolved contaminants in chamber 8 the exhaust stream from chamber 8. In yet other embodiments of this invention, particle analyzer 30 and/or other particle analyzers can be positioned elsewhere to, for example, monitor streams to and from applications in order to indicate whether the application process will render, or has rendered, acceptable results.

By sampling carbon dioxide stream 4 and directing subsequent aerosol 24 in a continuous fashion to particle analyzer 30, the process of detecting contaminants dissolved in the carbon dioxide stream 4 can be continuous in nature. In other embodiments, this invention provides for the detection of contaminants in carbon dioxide as it is fed to an application. In this manner, this invention provides for an online particle detection technique and system for the detection of contaminants in carbon dioxide in a real-time, continuous manner.

In certain applications, stream 24 can be analyzed by other light scattering techniques, such as classical particle counters which use classical applications of light scattering techniques. Whereas the single particle approach passes each individual particle or droplet sequentially through the incident beam, the classical approach detects the gross interaction of the source light with the aerosol as a whole. The method is based on the interaction of light with the aerosol cloud. This classical approach can be broken down into two subdivisions, turbidimetry and nephelometry.

In turbidimetry, the light source, the sample volume containing the aerosol undergoing testing, and a suitable detector are all located collinearly in the analyzer. The detector monitors the decrease in the intensity of the source light as it passes through the sample volume. This intensity decrease is due to the aerosol scattering some of the light out of the incident beam. The scattered light is then unable to reach the detector. The greater the concentration of aerosol in the sample volume, the greater the amount of scattered light and the greater the loss of intensity of the incident beam. In this approach, the incident beam's intensity is of greatest concern.

In nephelometry, the detector is located off of the axis defined by the light source and the sample volume. Typically, the detector is located 90 degrees off axis, although other configurations are known. In this configuration, the detector is responding to the amount of light scattered from the incident beam. In this case, the signal at the detector increases with the concentration of the aerosol as the amount of scattered light increases.

There is an advantage to using nephelometry as opposed to turbidimetry in applications where the concentrations of the resultant aerosols are expected to be low. Detecting a small signal from the scattered light against a dark background can be performed more accurately than detecting a small decrease in light intensity in a bright light source.

An example of a commercially available instrument utilizing the nephelometric approach in a continuous process analyzer is the HPM-1000 analyzer currently manufactured by MIE, Inc. (Bedford, Mass.). The instrument operates over a wide pressure range, is very rugged, and has a LOD of 1 $\mu g/m^3$ under optimal conditions. This equates to a LOD of about 1 ppb by weight or a number concentration of about $20\times10^6$ particles/$ft^3$, where said particle has a diameter greater than 0.1 μm, depending on the density of the test aerosol used for calibration, its specific particle size distribution, and the density of the process gas.

In another embodiment, the invention is directed to a method of detecting contaminants dissolved in a carbon dioxide stream, including the steps of a) sampling at least a portion of the carbon dioxide stream to form a carbon dioxide sample; b) modifying at least one physical condition of the carbon dioxide sample to form an aerosol that includes gaseous carbon dioxide and at least one suspended contaminant; c) detecting the number of particles of suspended contaminant of at least a portion of the particles of the aerosol with at least one first analyzer selected from the group consisting of a turbidimetry-based particle detector and a nephelometry-based particle detector; d) monitoring the number of detected particles relative to a preset value; and e) directing at least a portion of the aerosol, wherein said portion of the aerosol has a particle count below the preset level, to at least one particle counter. This method is particularly suited for lower purity carbon dioxide streams and/or if it is desirable to protect a single particle counter.

This method is illustrated with reference to FIG. 2. The process is similar to the one depicted in FIG. 1, only now first analyzer 34, which is robust to high levels of contamination, is used to protect particle analyzer 30 based on a predetermined reading from first analyzer 34. First analyzer 34 can operate, for example, based on the classical light detection techniques of nephelometry or turbidimetry. Particle analyzer 30 can be, for example, a particle counter such as a LPC or CNC, as discussed above.

When first analyzer 34 detects a level of contaminant in at least a portion of aerosol 24 which is above the predetermined value, first analyzer 34 sends a signal to valve 28 to halt the flow of aerosol 24 to particle analyzer 30. The predetermined value can be, for example, a level of contaminant that will overwhelm particle analyzer 30. Alternatively, the sample flow through first analyzer 34 can be stopped by other means such as turning off an internal sample pump or the external mass flow controller (not shown). These alternative approaches provide the functionality of valve 28, yet do not introduce particle-shedding upstream of particle analyzer 30.

Optional flow meter 36 measures the flow of aerosol 24 from first analyzer 34 and/or particle analyzer 30. Optional flow meter 36 can send a signal that results in an increase or decrease in the amount of carbon dioxide stream 4 sampled. For example, optional flow meter 36 could send a signal to pressure reduction device 22 or to another valve (not shown) which increases or decreases the amount of carbon dioxide stream 4 sampled.

One method for determining whether the carbon dioxide used in chamber 8 will at some point deposit an unacceptable amount of precipitated contaminants onto the workpiece is to heat and depressurize carbon dioxide sample 14 so that resulting aerosol 24 is at the same precipitation-forming conditions as carbon dioxide stream 4 eventually assumes during the actual process. However as discussed previously, some process conditions result in the formation of multiple phases in the carbon dioxide, such as the carbon dioxide snow cleaning processes. In those processes, a better particle count can be had by detecting aerosol 24 at a temperature slightly above the sublimation/boiling temperature of carbon dioxide at that pressure.

The concentration of contaminants dissolved in the carbon dioxide stream can be estimated by correlating a measured contaminant value with a known value. The known value can be obtained, for example, through the use of thermodynamic and solubility tables or through a calibration process. One example of a calibration process involves first expanding and/or heating carbon dioxide with a known concentration of contaminants in order to determine how many particles will actually precipitate and be detected during the analysis process. Once that value is known, a carbon dioxide sample with an unknown level of contaminant can be passed through the same conditions and directed to an analyzer to measure at least a portion of the precipitated contaminant. The measured value of precipitated contaminant can be measured against the known value in order to estimate the contaminant concentration in the carbon dioxide sample with an unknown level of contaminant.

The invention can be used to estimate the concentration of contaminants dissolved in a carbon dioxide stream. The method of estimating the concentration of contaminants includes the steps of a) sampling at least a portion of the carbon dioxide stream to form a carbon dioxide sample; b) modifying at least one physical condition of the carbon dioxide sample to form an aerosol that includes gaseous carbon dioxide and at least one suspended contaminant; c) detecting the number of particles of suspended contaminant of at least a portion of the total number of particles of the carbon dioxide sample with at least one particle counter to obtain a measured contaminant value; and d) correlating the number of particles of suspended contaminant detected of the portion of the total number of particles of the carbon dioxide sample to the number of particles of an equal portion of total number of particles of carbon dioxide with a known concentration of contaminants under the same physical conditions, thereby estimating the concentration of contaminants dissolved in the carbon dioxide stream. Additionally, a series of carbon dioxide samples with known concentrations of contaminants can be expanded through the analysis process to obtain a mathematical function which will give a more precise estimation of the concentration of contaminants dissolved in a carbon dioxide stream of unknown purity.

It is believed that the formation of the aerosol may be "path-dependent." In addition to the initial concentration of the dissolved contaminants and the final temperature and pressure of the aerosol, different aerosols can be formed from the same carbon dioxide stream if different methods are employed to form the aerosol. For example, it is believed that two aerosols at the same final pressure and temperature will have suspended particles that differ in both size and number if, for example, they each started at a different pre-expansion temperature or they each passed through a different sized orifice in the pressure reduction device. Even though both aerosols have identical final pressures and temperatures, their respective expansion and/or heating methods will determine their suspended contaminant size distribution.

This "path-dependent" nature of the precipitation mechanism is important because it affects the aerosol's particle distribution. The temperature and pressure changes used to create the aerosol should be chosen so that they lead to an aerosol with at least a portion of the suspended particles falling within the limit of detection of the detection technique employed. Generally, it is believed that in UHP applications, the formation of smaller sized particles is favored due to the low levels of NVRs in the carbon dioxide stream.

Figure 3:
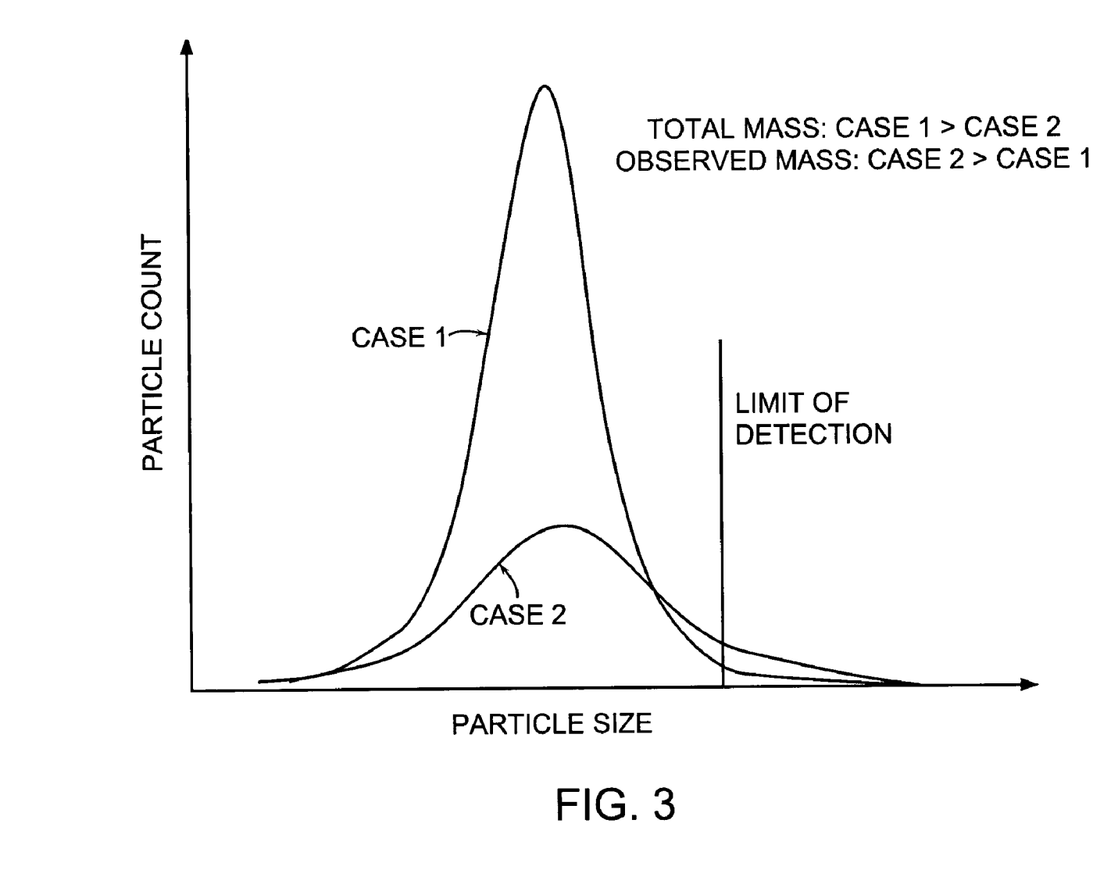
FIG. 3 is a graph illustrating the path-dependent nature of aerosol formation.

FIG. 3 illustrates the path-dependent nature of the contaminant precipitation mechanism, and how it can affect the methods of this invention. The carbon dioxide of Case 1 has a larger mass fraction of dissolved contaminants than does the carbon dioxide of Case 2. If the carbon dioxide of both Case 1 and Case 2 were used in the same process, with each undergoing the same path of expansion/heating, the carbon dioxide of Case 1 would result in more deposited contaminants on the workpiece than if the carbon dioxide of Case 2 is used. However if they underwent disparate paths of expansion/heating, it is possible that Case 1 would give a precipitate distribution where much of the precipitated particles are below the LOD. It is possible that during a particle detection process, the contaminants of the two carbon dioxides are precipitated in disparate manners, the measured values may lead to the erroneous conclusion that the carbon dioxide of Case 2 has less dissolved contaminant than the carbon dioxide of Case 1.

Since it is believed that precipitation is path-dependent, samples of carbon dioxide with unknown dissolved contaminant concentrations preferably are expanded and/or heated into an aerosol in the same manner that was used on the calibration samples. This allows a more accurate estimate of contaminant concentration and/or determination of whether the carbon dioxide stream used in the process will leave an acceptable level of deposited contaminants on the workpiece.

An alternative to calibrating with a carbon dioxide sample(s) of known concentration, is to determine a reference value which is known to give acceptable results in that particular process. Due to the path-dependent nature of the precipitation mechanism, this invention allows the monitoring of dissolved contaminants without determining the actual concentration in the carbon dioxide stream fed to a process. Accordingly, this invention includes a method for monitoring contaminants in a carbon dioxide stream that is directed to a workpiece, including the steps of a) identifying a reference value, wherein said reference value indicates that the dissolved contaminants will precipitate and deposit onto the workpiece in acceptably low levels, by detecting the number of particles of at least a portion of the dissolved contaminants in a calibration process which includes the steps of i) sampling at least a portion of an acceptable carbon dioxide stream to form an acceptable carbon dioxide sample; ii) modifying the conditions of the acceptable carbon dioxide sample to form an aerosol of gaseous carbon dioxide and precipitated contaminants, whereby at least a portion of the contaminants are in the form of suspended droplets; and iii) detecting the number of particles of at least a portion of the acceptable carbon dioxide sample with at least one particle counter; thereby identifying said reference value; b) subsequently directing a carbon dioxide stream to the workpiece; c) sampling said carbon dioxide stream to identify at least one measured value, wherein said measured value indicates whether contaminants will precipitate from the carbon dioxide stream and deposit onto the workpiece in an acceptably low level, by detecting the number of particles of an essentially equal portion of the dissolved contaminants as employed to determine the reference value in a monitoring process which includes the steps of: i) sampling at least a portion of said carbon dioxide stream to form a carbon dioxide sample; ii) modifying the conditions of the carbon dioxide sample to form an aerosol of gaseous carbon dioxide and precipitated contaminants; and iii) detecting the number of particles in the portion of the carbon dioxide sample with at least one particle counter; thereby identifying said measured values; and d) comparing the measured values with the reference value to determine the number of dissolved particles that will precipitate from the subsequently directed carbon dioxide and deposit onto the workpiece is an acceptably low level, thereby monitoring contaminants of the carbon dioxide stream.

Essentially, this method determines a reference value that is known to yield acceptable workpieces. Once that reference value is known, it can be used to determine whether any future carbon dioxide fed to that process will yield acceptable workpieces too. As long as the manner in which the aerosol is formed is not altered, the reference value can be used as an "upper bound" level against which future particle detection can be gaged. In this way, satisfactory results can be predicted without knowing the actual concentration of contaminants in either the acceptable carbon dioxide stream or the subsequent carbon dioxide streams.

Other detection devices can be used in combination with the methods and systems described herein. For example, a detection device based on piezoelectric principles, such as a SAW device, can be used. If the carbon dioxide stream is shown to be particle-free, the resonator may be used to measure the amount of NVR that condenses onto the cold sensor surface from the vapor phase. In this manner, a portion of the dissolved contaminant which does not precipitate to form the suspended particles can be detected and used to refine the concentration estimate. The sensitivity of the SAW device can be increased by up to a factor of 1,000 by increasing the oscillation frequency.

Another example of a detection device based on piezoelectric principals is a microcantilevers (MCs). MCs are mechanical devices made of tiny plates or leaf springs, typically 0.2–1 micrometer thick, 20–200 micrometers wide, and 100–500 micrometers long. Contaminants interact with the plates or leaf springs, producing MC bending and displacing a laser beam reflected from near the end of the cantilever. The mass of the interacting contaminant is determined by converting the displacement into an electronic signal by projecting the reflected laser beam onto a position-sensitive photodetector. One or more MCs can be used in combination with this invention to detect at least a portion of dissolved contaminants and provide a more accurate detection of contaminants.

Once it is known that the contaminant concentration is larger than a preset value, wherein said preset value indicates that an unacceptable amount of contaminant will be deposited onto the workpiece, remedial measures can be taken in order to avoid deposition of precipitated contaminants onto the workpiece. A further embodiment of the invention is directed to a method for supplying ultra-high purity carbon dioxide to a workpiece, including the steps of a) sampling at least a portion of the carbon dioxide stream to form a carbon dioxide sample; b) modifying at least one physical condition of the carbon dioxide sample to form an aerosol that includes gaseous carbon dioxide and at least one suspended contaminant; and c) detecting at least a portion of the suspended contaminant with at least one particle counter to obtain a measured contaminant value; d) comparing the measured contaminant value with a preset value; and e) removing at least a portion of the dissolved contaminant from the carbon dioxide stream when the measured contaminant value of the sample is larger than the preset value, thereby producing a stream of ultra-high purity carbon dioxide. The method of removing the dissolved contaminant can comprise a separation process, such as adsorption, absorption, catalytic oxidation, coalescent filtration, and/or distillation. Alternatively (or in addition to) a portion of carbon dioxide with a higher purity can be mixed with the carbon dioxide stream so that the mixture of the two has an acceptably low concentration of dissolved contaminant.

Another embodiment of the invention is directed to a method of detecting contaminants dissolved in a carbon dioxide stream, including the steps of a) sampling at least a portion of the carbon dioxide stream to form a carbon dioxide sample, wherein said carbon dioxide stream includes carbon dioxide with less than 10 ppb by weight dissolved particles of contaminants; b) modifying at least one physical condition of the carbon dioxide sample to form an aerosol that includes gaseous carbon dioxide and at least one suspended contaminant; and c) detecting the number of particles of suspended contaminant of at least a portion of the particles of the aerosol with at least one first analyzer selected from the group consisting of a turbidimetry-based particle detector and a nephelometry-based particle detector.

The invention will now be described in the following examples, which are not intended to be limiting in any way.

EXAMPLE 1

Aerosol Generation vs. Pressure

Figure 4:
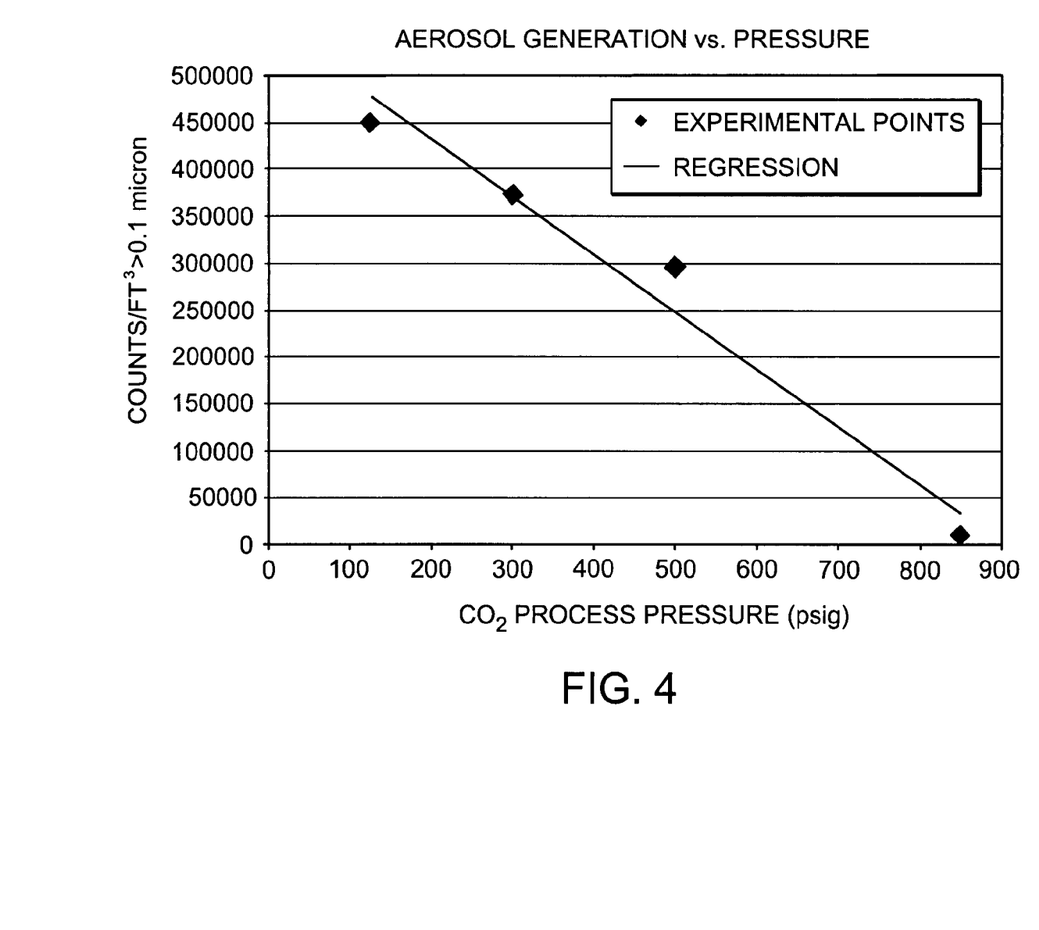
FIG. 4 is a graph illustrating the pressure dependent nature of aerosol formation.

FIG. 4 illustrates the pressure dependence of the generation of the aerosol. The sampling system used was that represented in FIG. 1 with a CGS-100 particle counter used as particle analyzer 30. Optional heater 20 was not employed.

Each data point in the graph is the average particulate concentration in carbon dioxide under a specific process pressure. The carbon dioxide process gas was supplied as vapor from an 850 psig cylinder source. The pressure of the carbon dioxide was controlled through an all metal valve to deliver the desired process pressure to the particle counter. All solid particles were removed by filtering the 850 psig supply immediately upstream of the throttling valve. As expected, the smallest number of particles was noted at a process pressure of 850 psig, a pressure at which the solubility of the carbon dioxide is greatest. A fairly linear relationship is obtained with the aerosol concentration increasing as the process carbon dioxide pressure decreases and along with it, the solubility of the NVR in the carbon dioxide.

The effect of the throttling valve on the particle count was assessed by running the same set of experiments in nitrogen, rather than carbon dioxide. No pressure dependence in the particle count was noted for when nitrogen was used. This indicates that shedding from the throttling valve was not responsible for the observed increase in particles during the carbon dioxide tests.

Finally, note that particulate concentration changes over a range of several thousand to several hundred thousand counts per cubic foot, for this set of experiments. Even the greatest concentration noted at 125 psig process pressure is still approximately a factor of 50× lower than the LOD of a conventional nephelometric-based analyzer. The ability to count single particles is therefore very important. This trend of aerosol concentration with process pressure would be unobservable without the use of the methods and systems outlined in this invention.

EXAMPLE 2

Aerosol Generation vs. Temperature

Liquid samples were withdrawn from four cylinders of carbon dioxide manifolded together. The pressure of the carbon dioxide in the cylinders was approximately 800 psig at room temperature. The sampling system used was that represented in FIG. 1. Optional heater 20 was used to modify the temperature of carbon dioxide sample 18 and pressure reduction device 22 dropped resulting aerosol 24 to approximately atmospheric pressure. Particle analyzer 30 was a Lasair 101.

Figure 5:
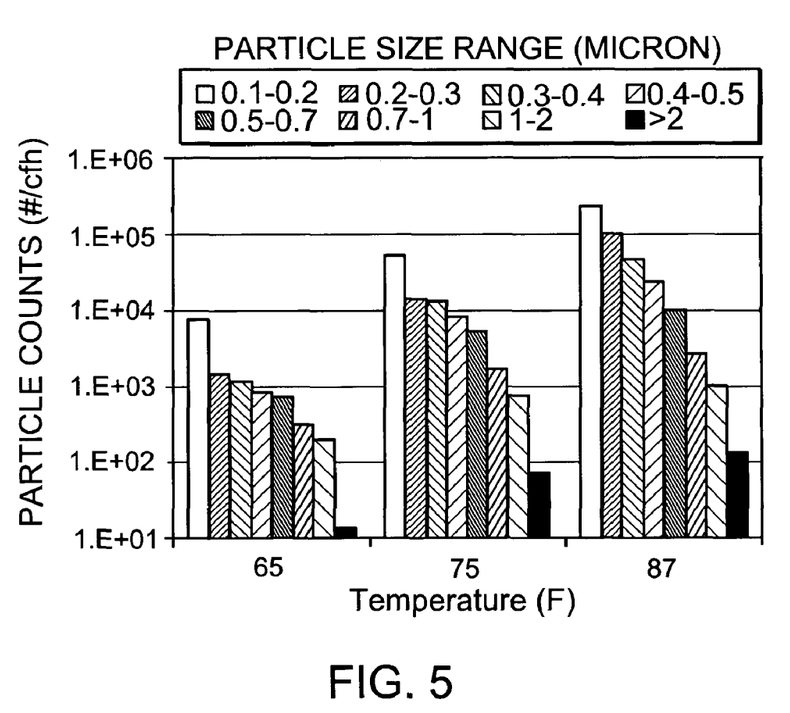
FIG. 5 is a graph illustrating the temperature dependent nature of aerosol formation.

Particle size distributions are shown in FIG. 5 at three different temperatures. The counts for each temperature represent the average values over a period of several hours. The impact of temperature on the particle size distribution from the same liquid source is significant. Note that the total number of particles counted generally decreases with temperature. This illustrates the path-dependent nature of the precipitation mechanism. While generally temperature decreases lower the solvency of the contaminant in carbon dioxide, the precipitation path employed can actually result in a larger number of the particles falling below the limit of detection. So a lower temperature can result in a decrease in the number of particles detected, even though a larger portion of the dissolved contaminants have actually precipitated.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of detecting contaminants dissolved in a carbon dioxide stream, comprising the steps of:

a) sampling at least a portion of the carbon dioxide stream in liquid or supercritical phase to form a carbon dioxide sample;

b) modifying at least one physical condition of the carbon dioxide sample to form an aerosol that includes gaseous carbon dioxide and at least one suspended contaminant; and c) detecting the number of particles of suspended contaminant, wherein the suspended contaminant is in the form of aerosol droplets, in at least a portion of the carbon dioxide sample with at least one particle counter.

2. The method of claim 1, wherein the step of modifying at least one physical condition includes increasing the temperature of the carbon dioxide sample to above the sublimation point of carbon dioxide at the pressure at which the suspended contaminant is detected.

3. The method of claim 2, wherein the step of modifying at least one physical condition includes increasing the temperature of the carbon dioxide sample to above the boiling point of carbon dioxide at the pressure at which the suspended contaminant is detected.

4. The method of claim 1, wherein the particle counter is at least one device selected from the group consisting of a white-light particle counter, a laser diode particle counter, a gas-powered laser particle counter, and a condensation nucleus counter.

5. The method of claim 4, wherein the suspended contaminant are detected by at least two of the devices selected from the group consisting of a white-light particle counter, a laser diode particle counter, a gas-powered laser particle counter, and a condensation nucleus counter.

6. The method of claim 4, wherein at least a portion of the suspended contaminant is detected by a piezoelectric device.

7. The method of claim 6, wherein the piezoelectric device is at least one device selected from the group consisting of a surface wave resonator and a microcantilever.

8. The method of claim 1, further including the step of directing the carbon dioxide sample through a filter prior to modifying at least one physical condition of the carbon dioxide sample to form an aerosol that includes gaseous carbon dioxide and at least one suspended contaminant.

9. The method of claim 1, further including the step of directing the carbon dioxide sample through a filter after modifying at least one physical condition of the carbon dioxide sample to form an aerosol that includes gaseous carbon dioxide and at least one suspended contaminant.

10. The method of claim 1, wherein the number of particles of suspended contaminant is detected at a pressure less than about 3,000 psia.

11. The method of claim 10, wherein the number of particles of suspended contaminant is detected at a pressure less than about 1,065 psia.

12. The method of claim 11, wherein the number of particles of suspended contaminant is detected at a pressure of about 14.7 psia.

13. The method of claim 1, wherein the carbon dioxide stream contains less than $1\times10^{-6}\%$ by weight dissolved contaminant.

14. The method of claim 13, wherein the carbon dioxide stream contains less than $1\times10^{-7}\%$ by weight dissolved contaminant.

15. A method for monitoring contaminants in a carbon dioxide stream that is directed to a workpiece, comprising the steps of:

a) identifying a reference value, wherein said reference value indicates that the dissolved contaminants will precipitate and deposit onto the workpiece in acceptably low levels, by detecting the number of particles of at least a portion of the dissolved contaminants in a calibration process which includes the steps of:

i) sampling at least a potion of an acceptable carbon dioxide stream to form an acceptable carbon dioxide sample;

ii) modifying the conditions of the acceptable carbon dioxide sample to form an aerosol of gaseous carbon dioxide and precipitated contaminants, whereby at least a portion of the contaminants are in the form of suspended droplets; and iii) detecting the number of particles of at least a portion of the acceptable carbon dioxide sample with at least one particle counter; thereby identifying said reference value;

b) subsequently directing a carbon dioxide stream to the workpiece;

c) sampling said carbon dioxide stream to identify at least one measured value, wherein said measured value indicates whether contaminants will precipitate from the carbon dioxide stream and deposit onto the workpiece in an acceptably low level, by detecting the number of particles of an essentially equal portion of the dissolved contaminants as employed to determine the reference value in a monitoring process which includes the steps of:

i) sampling at least a portion of said carbon dioxide stream to form a carbon dioxide sample;

ii) modifying the conditions of the carbon dioxide sample to form an aerosol of gaseous carbon dioxide and precipitated contaminants; and iii) detecting the number of particles in the portion of the carbon dioxide sample with at least one particle counter; thereby identifying said measured values; and d) comparing the measured values with the reference value to determine the number of dissolved particles that will precipitate from the subsequently directed carbon dioxide and deposit onto the workpiece is an acceptably low level, thereby monitoring contaminants of the carbon dioxide stream.

16. The method of claim 15, wherein the reference value indicates that the carbon dioxide stream contains less than $1 \times 10^{-6}$% by weight dissolved contaminant.

17. The method of claim 16, wherein the reference value indicates that the carbon dioxide stream contains less than $1 \times 10^{-7}$% by weight dissolved contaminant.

18. A system for continuously detecting contaminants dissolved in a carbon dioxide stream flowing through a solvent feed line, comprising:
a) a sampling means for removing a sample stream, wherein said sample stream is at least a portion of the carbon dioxide stream flowing through the solvent feed line;
b) a modification means in fluid communication with the sampling means, wherein said modification means modifies the conditions of the sample stream to form an aerosol of gaseous carbon dioxide and suspended contaminants;
c) at least one contaminant measurement zone in fluid communication with the modification means; and
d) at least one particle counting means, wherein said particle counting means can detect at least a portion of the suspended contaminants in the contaminant measurement zone with at least one particle counter.

19. The system of claim 18, further including a solids-removal means in fluid communication with the modification means, wherein said solids-removal means filters solid particles from the sample stream before the sample stream reaches at least one contaminant measurement zone.

20. The system of claim 18, further including a particle detecting means which can detect at least a portion of the suspended contaminants in at least one contaminant measurement zone with at least one turbidmetry-based particle detector.

21. The system of claim 18, further including a particle detecting means which can detect at least a portion of the suspended contaminants in at least one contaminant measurement zone with at least one nephelometry-based particle detector.

* * * * *